United States Patent [19]

Nelson et al.

[11] Patent Number: 5,759,166
[45] Date of Patent: Jun. 2, 1998

[54] IMMOBILIZING WRIST BRACE

[75] Inventors: Ronald E. Nelson, Chetek, Wis.; Karl E. Bjornson, Canton, Ohio

[73] Assignee: Tamarack International, Inc., Chetek, Wis.

[21] Appl. No.: 689,358

[22] Filed: Aug. 7, 1996

[51] Int. Cl.[6] .................................................. A61F 5/00
[52] U.S. Cl. ................................................ 602/21; 602/64
[58] Field of Search ........................ 602/5, 9, 20–21, 602/64; 473/59–63; 128/878, 879; D24/189, 190; D2/616, 617, 623

[56] References Cited

U.S. PATENT DOCUMENTS

| | | | |
|---|---|---|---|
| 3,369,258 | 2/1968 | Smith | 473/59 X |
| 4,013,070 | 3/1977 | Harroff | 602/21 |
| 4,441,490 | 4/1984 | Nirsch | 602/21 |
| 4,584,993 | 4/1986 | Nelson | 128/77 |
| 4,716,892 | 1/1988 | Brunswick | 602/21 |
| 4,854,309 | 8/1989 | Elsey | 602/21 |
| 5,160,314 | 11/1992 | Peters | 602/21 |
| 5,267,943 | 12/1993 | Darcyger | 602/5 |
| 5,415,624 | 5/1995 | Williams | 602/21 |
| 5,538,500 | 7/1996 | Peterson | 602/20 X |
| 5,667,484 | 9/1997 | Brossard | 602/21 |

*Primary Examiner*—Richard J. Apley
*Assistant Examiner*—Denise Pothier
*Attorney, Agent, or Firm*—Nawrocki, Rooney & Sivertson, P.A.

[57] ABSTRACT

An immobilizing wrist brace in the form of a base conformable as a sleeve to a human wrist and including a longitudinal support member adapted to overlie the anterior portion of a wrist, the support member including a distal extension adapted to extend into the palmar area of the hand. A pair of anchor straps are fitted to the distal extension and extend therefrom in generally opposite directions to fit around different portions of the hand to allow ambidextrous use of the brace. A pair of straps encircle the brace to enhance wrist immobilization.

13 Claims, 2 Drawing Sheets

IMMOBILIZING WRIST BRACE

BACKGROUND OF THE INVENTION

This invention relates generally to the field of orthopedic braces, more particularly to elastic support braces, and still more particularly to elastic wrist braces.

DESCRIPTION OF THE PRIOR ART

Those of skill in the art of the present invention well recognize the complexity of the bone and muscle structure of the hand and wrist, and how highly prone to injury this structure has proven to be. Simple over-exertion, hyperextension, or unusual rotary or lateral movement may cause injury to the wrist. Such injury may require that the wrist be supported and in some cases, immobilized.

Numerous wrist supports are known in the prior art. For example, a wrap of tape or elastic material may be employed for simple wrist support. A more advanced support typically includes a base of supportive elastic material adapted to be positioned around the wrist together with positioning and/or supporting straps as well as a variety of stays or braces to restrict movement of the wrist.

In some instances it is desired to immobilize the wrist without resort to a cast. In these instances, it is common to employ a palmar spoon, with or without additional support structures. Such supporting structures—particularly those employing a palmar spoon—must be positively anchored across the wrist to be effective. An ambidexrous wrist brace would be an economic benefit by reducing manufacturing and inventory costs.

SUMMARY OF THE INVENTION

An apparatus in accordance with the present invention provides an improved brace with structure for immobilizing the wrist. Additional structure is provided to make the brace ambidextrous, that is, it may be used on either the left or right wrist.

Briefly described, a brace in accordance with the present invention comprises a base formed as a sleeve from a generally flat sheet of flexible, at least partially elastic material. A plurality of support members are mounted on the base, including a longitudinally aligned center support element. In a preferred embodiment, the center support element is a palmar spoon which lies over the middle of the proximal side of the wrist when the base is on the wrist, and has a distal extension which reaches into the palm area of the hand. The center support element is maintained within an internal pocket and has a rounded or hemispherical projection at its distal end that is positioned over the lunate bone in the palm and preferably exerts a pressure on the lunate bone.

A pair of positioning straps extend in generally opposite directions from the distal end of the center support pocket. The positioning straps are wrapped around the hand and fastened to the base to keep the brace centered on the wrist. The configuration of the positioning straps enables the apparatus of this invention to be ambidextrous, that is, the brace can be used on the right or left wrist. A non-elastic anchor strap at the proximal portion of the brace firmly anchors the brace to the arm adjacent the wrist while a partially elastic anchor strap circles the wrist to apply immobilizing pressure to the center support element. A second stay carried by the brace is adapted to lie along the dorsal side of the wrist to provide additional immobilization in cooperation with the anchor straps.

BRIEF DESCRIPTION OF THE DRAWINGS

The objects of the present invention and many of the attendant advantages of the present invention will be readily appreciated as the same become better understood by reference to the following detailed description when considered in connection with the accompanying drawings, in which drawings like reference numerals designate like parts through the figures thereof and wherein.

DETAILED DESCRIPTION OF THE PREFERRED EMBODIMENTS

Figure 1:
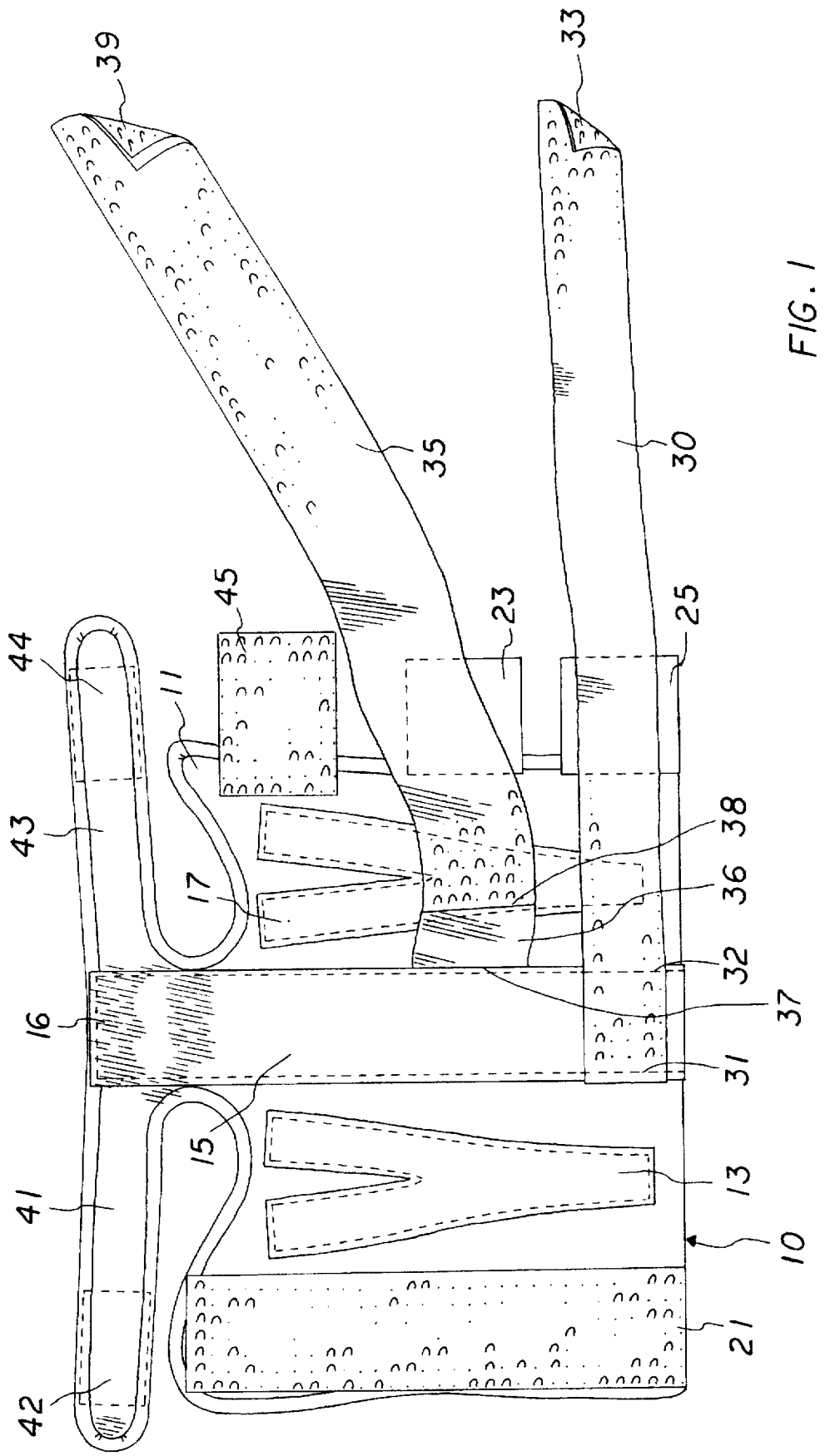
FIG. 1 is a plan view of a wrist brace in accordance with the present invention.

FIG. 1 illustrates a wrist brace indicated at 10, including an elastic base 11 comprising a generally flat sheet of a flexible, at least partially elastic material, and a set of fastening means such as tabs 23, 25 and 45 fixed to one side of base 11. The tabs 23, 25 and 45 mate with a fastening pad 21 on the opposite side of base 11, to adjustably conform and hold base 11 around a wrist as a sleeve, in known manner. Also shown fixed to base 11 are flexible, inelastic longitudinal support members 13 and 17 designed to restrict undesired flexion, extension and rotation of the wrist. The support members 13 and 17 may be formed as pockets containing stay elements and may take any desired configuration—a "Y" configuration being illustrated. It should be noted that in the preferred embodiment of this invention, all fastening elements are preferably of the hook-and-loop type well known to those familiar with the art.

A central support member 15 is centered on the proximal side of base 11 such that when base 11 is conformed to a wrist, member 15 will overlie the anterior side of the wrist. Member 15 includes a distal extension 16, and may be formed as a pocket in which is disposed an inflexible and inelastic stay element such as a palmar spoon (See stay 40 of FIG. 2), the pocket of member 15 being open at its proximal end for insertion and removal of a stay, in known manner.

Fastening pad 21 may be formed of a sheet of loop fastening material stitched to the base 11 to define a pocket. A rigid dorsal/posterior stay element is preferably contained within the pocket of pad 21 to cooperate with the stay element in member 15 for wrist immobilization. The non-visible sides of tabs 23, 25 and 45 may be formed of pads of hook material to cooperate with pad 21. The visible face of tab 45 is formed by a pad of loop material, as shown.

FIG. 1 also shows a pair of support straps 30 and 35. Strap 30 is fixed at one end to center support member 15 as by a pair of seams 31 and 32. The free end of strap 30 carries a fastening tab 33 for adjustable fastening to other fastening means carried along the length of strap 30. Strap 35 has one end connected to one side of an elastic segment 36 along a seam 38. Another side of segment 36 is connected to or adjacent support member 15 by a seam 37. The free end of strap 35 carries a fastening tab 39 for adjustable fastening to other fastening means carried along the length of strap 35.

In practice, when base 11 has been conformed to a wrist, and supported on the wrist as a sleeve by cooperation of tabs 23, 25 and 45 with pad 21, additional support and migration control is provided by wrapping each of straps 30 and 35 around base 11 and fastening each in place. The body of straps 30 and 35 are preferably of an inelastic material and may be formed of a strip of loop fastener material. Inflexible strap 30 firmly anchors the base, including the stay elements within the pockets of member 15 and pad 21 to the arm adjacent the wrist. It has been found that the use of elastic segment 36 to connect upper strap 35 to or adjacent to one side of center support member 15 will facilitate immobilization of the wrist beyond that attainable by a wholly inflexible strap or an elastic strap overlying the immobilizing stay elements of member 15 and pad 21.

Also shown in FIG. 1 are a pair of anchor straps 41 and 43. Each of straps 41 and 43 have one end permanently connected to distal end of base 11, preferably to the extension 16 of support member 15. The free end of straps 41 and 43 carry fastening pads 42 and 44, respectively, on their non-visible face, the pads 42 and 44 being shown in phantom as viewed through the straps 41 and 43 and being a pad of hook material. The straps 41 and 43 are shown extending from distal extension 16 of member 15 in generally opposite directions, the distal extension 16 allowing straps 41 and 43 to extend from the palmar area of the hand to encompass or wrap around different portions of the hand. Dependent on the hand (left or right) to which the brace is applied, one of the straps 41 and 43 will wrap from the palm and pass between the finger and thumb and engage pad 45. The other of straps 41 and 43 wraps from the palm and generally around the ulnar border at the base of the little finger to engage pad 45. As will be evident to those familiar with the art, the brace of this invention is anchored and centered by straps 41 and 43, as they wrap around opposing planar borders to be secured to the base of the brace on the dorsal/posterior side of the wrist. It should be specifically noted that the configuration of straps 41 and 43 allows for ambidextrous use of brace 10, that is, brace 10 may be used on either a right or left wrist. In the illustrated embodiment, the straps are symmetrical with regard to the centerline of the pocket of pad 15 and, in particular, to the centerline of its extension 16. Indeed, that portion of base 11 in proximity to the distal portion 16 is symmetrical to facilitate ambidextrous use of the brace.

Figure 2:
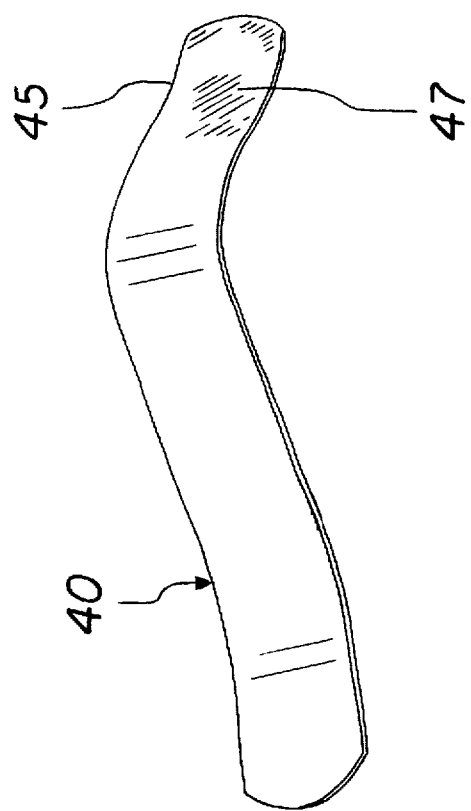
FIG. 2 is a side plan view of a preferred embodiment of a palmar spoon used as a stay element in the wrist brace of FIG. 1.

Referring now to FIG. 2, there is shown a side plan view of a stay 40 generally conforming to the known palmar spoon, the stay 40 being adapted to be placed within a pocket of center support member 15 of FIG. 1, such that a distal "spoon" end 45 of stay 40 will lie within distal extension 16. Thus, spoon 45 will also be adapted to extend into the proximal palmar area of the hand in known manner. As shown in FIG. 2, stay 40 has, along its major length, a gentle curve adapted to generally conform to the curve of the anterior side of a wrist to avoid unnecessary discomfort when pressure is applied to the wrist by brace 10. It can also be seen that spoon end 45 of stay 40 curves downward to generally fit into the concave palmar area above the lunate bone when pressure is applied to member 15. A rounded or hemispherical projection 47 is preferably formed within end 45 to facilitate positioning of spoon end 45 as it is pressed into the palmar area above the concave lunate bone.

Having thus described the preferred embodiments of the present invention, those of skill in the art will readily appreciate the other useful embodiments within the scope of the claims hereto attached.

What is claimed is:

1. In a wrist brace for immobilization of a human wrist of the type having a base formed of at least partially elastic materials, the base being adapted to be formed into a sleeve surrounding either a left or right wrist and carrying an anterior stay having a longitudinal axis adapted to extend along the wrist with the stay having a distal portion configured to lie within the palm of a hand, the improvement which comprises a pair of anchoring straps extending generally symmetrically in opposing directions relative to the longitudinal axis of said stay to free ends, said straps being offset distally from the region of the stay distal portion, and including means carried at the free ends of said anchoring straps and carried on said base for securing said straps to said base around opposing palmar borders, said borders being the ulnar border at the base of the little finger and the border between the fingers and thumb.

2. The wrist brace improvement of claim 1 further comprising first and second wrist straps anchored to said base each being adapted to encircle said sleeve and having a free end, said wrist straps including attachment means for securing the free ends to their associated strap, and also comprising hook and loop attachment means for securing said sleeve by attaching opposed overlapped edges of said base together, such that said sleeve is adapted to encircle the wrist when secured by said attachment means.

3. The wrist brace improvement at claim 2 wherein said first strap is inelastic and encircles said sleeve of the proximal portion thereof.

4. The wrist brace improvement of claim 3 wherein said second strap includes an elastic segment and an inelastic segment and encircles said sleeve intermediate the anterior stay distal portion and the first strap.

5. The wrist brace of claim 4 wherein second strap elastic portion interconnects the base and the second strap inelastic portion.

6. The wrist brace improvement of claim 5 wherein said first and second straps overlie said anterior stay and said dorsal stay when said first and second straps encircle said sleeve.

7. The wrist brace improvement of claim 1 further comprising first and second wrist straps anchored to said base each being adapted to encircle said sleeve and having a free end, said wrist straps including attachment means for securing the free ends to their associated strap, and also comprising hook and loop attachment means for securing said sleeve by attaching opposed overlapped edges of said base together, such that said sleeve is adapted to encircle the wrist when secured by said attachment means.

8. The wrist brace improvement at claim 7 wherein said first strap is inelastic and encircles said sleeve at the proximal portion thereof.

9. The wrist brace improvement of claim 8 wherein said second strap includes an elastic segment and an inelastic segment and encircles said sleeve intermediate the anterior stay distal portion and the first strap.

10. The wrist brace of claim 9 wherein second strap elastic portion interconnects the base and the second strap inelastic portion.

11. The wrist brace improvement of claim 10 wherein said first and second straps overlie said anterior stay and said dorsal stay when said first and second straps encircle said sleeve.

12. The wrist brace improvement of claim 1 wherein the distal portion of said base is generally symmetrical with respect to the longitudinal axis of said anterior stay.

13. The wrist brace improvement of claim 1 wherein said anchoring straps are generally symmetrical with respect to said anterior stay.

* * * * *